United States Patent
Satzinger et al.

[11] Patent Number: 4,698,341
[45] Date of Patent: Oct. 6, 1987

[54] USE OF 1,6-NAPHTHYRIDINONE DERIVATIVES IN TREATING PULMONARY THROMBOSIS

[75] Inventors: Gerhard Satzinger, Denzlingen; Johannes Hartenstein, Stegen-Wittental; Karl Mannhardt, Elzach-Oberprechtal; Jürgen Kleinschroth, Denzlingen; Manfred Herrmann; Edgar Fritschi, both of St. Peter; Horst-Dietmar Tauschel, Ettenheim; Bernd Wagner, Denzlingen; Günter Wolf, Freiburg, all of Fed. Rep. of Germany

[73] Assignee: Gödecke Aktiengesellschaft, Berlin, Fed. Rep. of Germany

[21] Appl. No.: 753,758

[22] Filed: Jul. 11, 1985

Related U.S. Application Data

[63] Continuation-in-part of Ser. No. 635,315, Jul. 27, 1984.

[30] Foreign Application Priority Data

Jul. 30, 1983 [DE] Fed. Rep. of Germany ....... 3327650
Jan. 29, 1985 [DE] Fed. Rep. of Germany ....... 3502831

[51] Int. Cl.$^4$ ................. A61K 31/455; A61K 31/535; C07D 471/04
[52] U.S. Cl. .................................... 514/230; 514/232; 514/236; 514/300; 546/123; 544/127
[58] Field of Search ................ 546/123; 514/300, 230, 514/232, 236; 544/127

[56] References Cited

U.S. PATENT DOCUMENTS

| | | | |
|---|---|---|---|
| 4,154,837 | 5/1979 | Heider | 546/141 |
| 4,304,914 | 12/1981 | Schroff et al. | 546/123 |
| 4,329,349 | 11/1982 | Sandoz | 546/316 |
| 4,370,334 | 1/1983 | Sato | 546/321 |

FOREIGN PATENT DOCUMENTS 0133530 2/1985 European Pat. Off. .

Primary Examiner—Henry R. Jiles
Assistant Examiner—Dale A. Bjorkman
Attorney, Agent, or Firm—Elizabeth M. Anderson

[57] ABSTRACT

New 1,6-naphthyridinone derivatives of the formula I

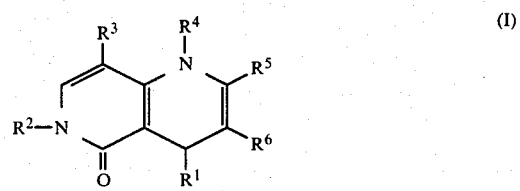

are herein described wherein
$R^1$ represents an unsubstituted or substituted aromatic or heteroaromatic ring;
$R^2$ is hydrogen, a straight-chained or branched alkyl, alkoxyalkyl, or a substituted or unsubstituted aminoalkyl group with up to ten carbon atoms;
$R^3$ is hydrogen, a straight-chained or branched alkyl group, or an alkoxycarbonyl radical with up to four carbon atoms;
$R^4$ is hydrogen, or a morpholinoethyl group;
$R^5$ is a straight-chained or branched alkyl group with up to four carbon atoms, or an amino group; and
$R^6$ is a carboxyl group, or an alkyl- or alkyloxyalkyl carbonyl radical, containing up to 12 carbon atoms and optionally interrupted by an oxygen, sulphur, or nitrogen atom;

as well as optionally the pharmacologically acceptable salts thereof; processes for the preparation of these derivatives and their use in the control of vascular diseases.

2 Claims, No Drawings

USE OF 1,6-NAPHTHYRIDINONE DERIVATIVES IN TREATING PULMONARY THROMBOSIS

CROSS REFERENCE TO RELATED APPLICATION

This is a continuation-in-part application of U.S. Ser. No. 635,315 filed July 27, 1984.

SUMMARY OF THE INVENTION

The invention concerns new 1,6-naphthyridinone derivatives of the formula I

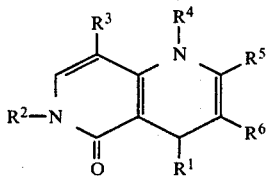

wherein
$R^1$ represents an unsubstituted or substituted aromatic or heteroaromatic ring;
$R^2$ is hydrogen, a straight-chained or branched alkyl, alkoxyalkyl, or a substituted or unsubstituted aminoalkyl group with up to ten carbon atoms;
$R^3$ is hydrogen, a straight-chained or branched alkyl group, or an alkoxycarbonyl radical with up to four carbon atoms;
$R^4$ is hydrogen, or a morpholinoethyl group;
$R^5$ is a straight-chained or branched alkyl group with up to four carbon atoms, or an amino group; and
$R^6$ is a carboxyl group, or an alkyl- or alkyloxyalkyl carbonyl radical, containing up to 12 carbon atoms and optionally interrupted by an oxygen, sulphur, or nitrogen atom;
as well as the pharmacologically acceptable salts thereof.

The invention further concerns a process for the preparation of 1,6-naphthyridinone derivatives of the formula I, characterized in that either
(a) a dihydropyridine of the formula IX

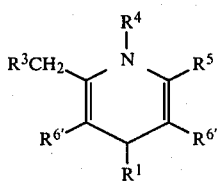

wherein $R^1$, $R^3$, $R^4$, and $R^5$ have the above stated meanings and $R^{6'}$ represents an alkoxycarbonyl radical of the formula V, is reacted with s-triazine in the presence of a base;
(b) a 1,4-dihydropyridine of the general Formula IX is reacted together with a dialkylformamide-dialkylacetal of the formula X

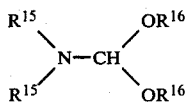

wherein the radicals $R^{15}$ may be the same or different and represent a methyl or ethyl group, and the radicals $R^{16}$ each represent an alkyl group with up to four carbon atoms, or together represent an alkylene group with up to three carbon atoms, and that the compounds of the formula XI

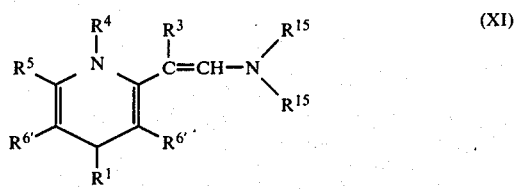

thus obtained, wherein $R^1$, $R^3$, $R^4$, $R^5$, $R^{6'}$, and $R^{15}$ have the meanings stated above, are reacted with ammonia, or
(c) 2,4-dihydroxypyridine is reacted together with a compound of the formula XII

wherein $R^1$ and $R^{6'}$ have the above stated meanings and $R^{5'}$ represents a straight-chained or branched alkyl group with up to four carbon atoms, in the presence of ammonia.

DETAILED DESCRIPTION

Preferred are 1,6-naphthyridinone derivatives of the formula I, wherein
$R^1$ represents an unsubstituted or substituted phenyl radical, substituted, preferably in two or three position, by halogen, such as fluorine, chlorine, or bromine, nitro, methyl, methoxy, difluoromethoxy, trifluoromethoxy, cyano, amino, mono- or dialkylamino having up to six carbon atoms, for example dimethylamino or diethylamino, methylthio, or trifluoromethyl, or disubstituted, preferably in 2,3 positions by methoxy or methylenedioxy, or in 2,3 or 2,6 positions by halogen atoms, as defined above, which may be the same or different, an unsubstituted pyridyl, thienyl, or 2,1,3-benzoxadiazolyl radical;
$R^2$ is hydrogen, an alkyl group containing up to six carbon atoms, for example, a methyl, ethyl, n-propyl, or isopropyl radical, an alkoxyalkyl group of the formula II $$-(CH_2)_n-O-R^7 \qquad (II)$$

wherein $R^7$ represents a straight-chained or branched alkyl group having up to six carbon atoms, and n is an integer 2 or 3, or an aminoalkyl group of the formula III

wherein $R^8$ and $R^9$ may be the same or different and represent a straight-chained or branched alkyl group having up to six carbon atoms, or together form an alkylene group containing four to six carbon atoms, and n equals two or three;

$R^3$ represents hydrogen, a methyl, ethyl, or isoproyl group, or an alkoxycarbonyl radical of the formula IV $$-CO_2R^{10} \qquad (IV)$$

wherein $R^{10}$ represents a methyl, ethyl, propyl, or isopropyl group;
$R^4$ is hydrogen or a morpholinoethyl group;
$R^5$ is a methyl or ethyl radical, or an amino group;
$R^6$ is a carboxyl group or an alkoxycarbonyl radical of the formula V $$-CO_2R_{11} \qquad (V)$$

wherein $R^{11}$ represents either a methyl, ethyl, n-propyl, isopropyl, n-butyl, isobutyl, sec. butyl or tert. butyl radical, an alkoxyalkyl or alkylthioalkyl group of the general formulae VI and VII $$-(CH_2)_n-O-R^{12} \qquad (VI)$$

$$-(CH_2)_n-S-R^{12} \qquad (VII)$$

or an aminoalkyl group of the formula VIII

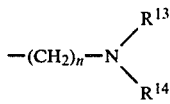

(VIII)

wherein $R^{12}$ represents a straight-chained or branched alkyl group having up to six carbon atoms,
and $R^{13}$ and $R^{14}$ may be the same or different and represent hydrogen, a straight-chained or branched alkyl group having up to six carbon atoms or a benzyl group, or together form an alkylene group having four to six carbon atoms, and n equals two or three.

Also preferred are 1,6-naphthyridinone derivatives of the formula IA

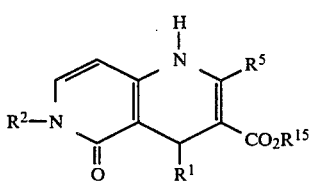

(IA)

wherein $R^1$ is a phenyl or phenyl substituted in the 2- or 3-positions by fluorine, chlorine, bromine, amino, nitro, trifluoromethyl, methoxy, difluoromethoxy, trifluoromethoxy, cyano, dimethylamino or diethylamino, or a pyridyl or thienyl radical, $R^2$ is hydrogen, an alkyl or alkoxy alkyl group containing up to six carbon atoms or an alkylamino alkyl group of the formula III

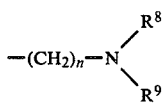

(III)

wherein $R^8$ and $R^9$ may be the same or different and represent a straight-chained or branched alkyl group having up to six carbon atoms or represent together an alkylene group containing four to six carbon atoms, n represents the integers 2 or 3, $R^5$ is an amino group or a methyl or ethyl group, and $R^{15}$ represents a hydrogen atom or a straight-chained, branched or cyclic alkyl or alkoxyalkyl-radical containing up to six carbon atoms; as well as the pharmacologically acceptable salts thereof.

Still also preferred are the compounds of Formula IA, in which $R^2$ represents a hydrogen atom or an alkyl group containing up to four carbon atoms.

The compounds of formula I show valuable pharmacological properties with favorable general tolerance.

Due to their vasospasmolytic and thrombocyte aggregation-inhibiting effects they are especially indicated for cerebral, cardiac, and peripheral vascular diseases, such as myocardial ischemia, for cerebral infarction, pulmonary thrombosis and for atherosclerosis and other symptoms of a stenosis, in particular since there are almost no negatively inotropic side effects compared with other known preparations of similar mode of action. The 1,6-naphthyridinone derivatives of the present invention are therefore valuable agents for controlling the cardiovascular mortality which amounts at present to more than 50% of all deaths in Germany. Another subject of the present invention is therefore the use of 1,6-naphthyridinone derivatives of the formula I for controlling vascular diseases.

The compounds of formula I with $R^5=NH_2$ are prepared according to process (a) from the corresponding 2-aminodihydropyridines of the formula IX with $R^5=NH_2$.

The compounds of the formula XIII

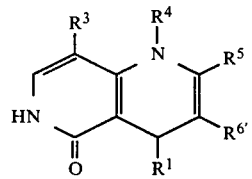

(XIII)

thus obtained, wherein $R^1$, $R^3$, $R^4$, $R^5$, and $R^{6'}$ have the above stated meaning, if desired are N-alkylated, N-aminoalkylated, or N-alkoxyalkylated in a generally known manner with a compound of the formula XIV $$X-R^{2'} \qquad (XIV)$$

wherein $R^{2'}$ represents a straight-chained or branched lower alkyl group, an alkoxyalkyl group of the formula II or an aminoalkyl group of the formula III.

Compounds of the formula I, in which $R^6$ represents a carboxyl group, are prepared by hydrolyzing in a previously known manner compounds of the formula I, in which $R^6$ represents an alkoxycarbonyl radical suitable for the splitting of esters, preferably in an acid medium.

The reaction of s-triazine with the compounds of the formula IX (process a) has to be considered surprising since the literature [Chem. Rev., 82, (1982)] shows that during treatment of 1,4-dihydropyridines with strong bases such as sodium hydride the proton at the nitrogen atoms is removed forming a sodium amide which then further reacts, e.g., with alkyl halides to form N-alkyl derivatives. The expected reaction does not occur in this case but an aminomethenylation takes place at the methyl group and produces the compounds of formula XIII.

The 1,4-dihydropyridines of the formula IX used for process (a) and (b) are known [cf., e.g., Chem. Rev., 82, (1982) p. 223] or can be prepared analogously.

Process (c) also is chemically novel since it has to be considered surprising that 2,4-dihydroxypyridine reacts in the manner described.

The compounds of the formula XII are known or may be prepared according to processes known from literature [Org. Reactions, Vol. 15 (1967) p. 204 ff]. 2,4-Dihydroxypyridine is commercially available.

In order to perform reaction (a) the 1,4-dihydropyridine derivative is heated together with s-triazine to temperatures of 50°–160° C., preferably 100°–150° C., in an inert organic solvent in the presence of strong bases such as, e.g., alkali alcoholates or sodium hydride in an inert organic solvent. Suitable solvents are mainly polar solvents such as dimethylsulfoxide, dimethylformamide, ethyleneglycol dimethylether, or lower alcohols such as ethanol.

In order to perform the reaction according to the process variant (b) the corresponding 1,4-dihydropyridine derivative is reacted with an equivalent or excessive quantity of dialkylformamide-dialkylacetal, preferably in the presence of an aprotic solvent such as dimethylformamide, dimethylsulfoxide or hexamethyl phosphoric acid triamide, while heating. Suitable formamide acetals are mainly dimethylformamide-dimethylacetal and dimethylformamide-diethylacetal.

The intermediate product of the formula XI obtained according to the process variant (b) is transferred to compounds of the formula XIII by reaction with ammonia in the presence of a solvent, preferably protic, at room temperature or at a higher temperature, preferably at the boiling temperature of the solvent used. Suitable solvents are mainly lower alcohols such as methanol or ethanol.

Reaction (c) is preferably performed in inert organic solvents, in particular lower alcohols such as, e.g., methanol, ethanol, or isopropanol. It is equally suitable to perform the reaction at higher temperatures, preferably at the boiling temperature of the solvent used. The products of the reaction can be isolated and purified according to known separation methods such as crystallization and/or chromatography.

The compounds of the formula XIII are N-alkylated, N-aminoalkylated, and N-alkoxyalkylated according to previously known methods, preferably using a hydrohalogenide acceptor. If suitable conditions are chosen for the reaction its course shows a high regional selectivity. The products are separated and/or purified by means of chromatography and/or crystallization.

For purification purposes and pharmacotechnological reasons acid or basic compounds of the formula I, which for $R^6$ show a carboxyl group, or a substituted or unsubstituted aminoalkoxycarbonyl radical, or for $R^2$ a substituted or unsubstituted aminoalkyl group, and/or for $R^5$ an unsubstituted or substituted amino group, are preferably transferred into crystalline, pharmacologically acceptable salts.

If $R^6$ represents a carboxyl group the corresponding pharmacologically acceptable salts of the alkali or alkaline earth metals can be prepared by means of bases such as, e.g., hydroxides or carbonates. If the radicals $R^2$, $R^5$, and $R^6$ display basic properties the pharmacologically acceptable salts are obtained in the usual way by means of neutralization of the bases with corresponding inorganic or organic acids. Suitable acids are, e.g., hydrochloric acid, sulphuric acid, phosphoric acid, hydrobromic acid, acetic acid, tartaric acid, lactic acid, citric acid, malic acid, salicylic acid, ascorbic acid, malonic acid, or succinic acid.

Since the compounds of the formula I according to the invention are showing a chiral center at C-4 they may be present either as racemic mixtures or in the form of the enantiomers.

The compounds of the formula I according to the invention may be applied in liquid or solid form, orally or parenterally. For the injectionsolution mainly water is used containing such additives as stabilizers, solubilizers, or buffers as are usual for injection-solutions.

Such additives are, e.g., tartrate and citrate buffers, ethanol, complex former (such as ethylenediamine tetraacetic acid and the nontoxic salts thereof), as well as high molecular weight polymers (such as liquid polyethyleneoxide) to regulate the viscosity. Solid vehicles are, e.g., starch, lactose, mannitol, methyl cellulose, talcum highly dispersed silicic acids, higher molecular weight fatty acid (such as stearic acid), gelatin, agar-agar, calcium phosphate, magnesium stearate, animal and vegetable fats, solid high molecular weight polymers (such as polyethylene glycol); if desired preparations suited for oral application may in addition contain flavors and/or sweetening agents.

Enterally administered single doses are in the order from about 5 to 250 mg; preferably 20–100 mg. Doses for parenteral application are in the order from about 1 to 20 mg.

The following examples serve to illustrate the invention further.

EXAMPLE 1

1,4,5,6-Tetrahydro-2-methyl-4-(3-nitrophenyl)-5-oxo-1,6-naphthyridine-3-carboxylic acid ethyl ester

Variant a

A suspension of 2.4 g (9 mmol) 3-nitrobenzylidene acetoacetic acid ethyl ester and 1.0 g (9 mmol) 2,4-dihydroxypyridine in 25 ml ethanol is saturated with ammonia gas at room temperature. The suspension is heated for five hours at boiling temperature by continuing the supply of gaseous ammonia. After removing the solvent in a vacuum the residue is dissolved in 50 ml chloroform while heating. The crystals precipitating during cooling are filtered off by suction and purified by crystallization from ethanol/ethyl acetate 1:1. There is obtained 1,4,5,6-tetrahydro-2-methyl-4-(3-nitrophenyl)-5-oxo-1,6-naphthyridine-3-carboxylic acid ethyl ester as yellow needles with a melting point of 285° C. (decomposition).

Variant b

A solution of 56.5 g (150 mmol) 1,4-dihydro-2,6-dimethyl-4-(3-nitrophenyl)pyridine-3,5-dicarboxylic acid diethyl ester in 250 ml dimethylformamide is added dropwise into a suspension of 4.95 g (165 mmol) sodium hydride (80% in paraffin oil) in 75 ml dry dimethylformamide under nitrogen atmosphere.

When the gas development has weakened the mixture is heated to 60° C. for a short time (approximately ten minutes) and 12.2 g (150 mmol) s-triazine in 250 ml dimethylformamide are added dropwise. The reaction mixture is heated for 16 hours at boiling temperature, filtered after cooling and concentrated in a vacuum. The dark residue is boiled in 400 ml n-hexane. The undissolved raw product is suspended in 500 ml hot ethanol after decanting off the n-hexane and applied to a column with silica gel. Subsequently elution is carried out with methylene chloride/methanol.ammonia (9:1 v/v) and the desired fraction is recrystallized twice from ethanol/ethyl acetate (1:1 v/v) for further purification. There is obtained 1,4,5,6-tetrahydro-2-methyl-4-(3-nitrophenyl)-5-oxo-1,6-naphthyridine-3-carboxylic acid ethyl ester in a form of yellow needles with a melting point of 285° C. (decomposition).

In an analogous manner, as described in variant (a), the following compounds are obtained.

(±)-4-(2-Diethylaminophenyl)-6-ethyl-1,4,5,6-tetrahydro-2-methyl-5-oxo-1,6-naphthyridine-3-carboxylic acid methyl ester, mp 214°–215° C. (from ethyl acetate);

(±)-2-Amino-1,4,5,6-tetrahydro-4-(2-nitrophenyl)-5-oxo-1,6-naphthyridine-3-carboxylic acid ethyl ester, mp 300° C. (decomp.) (from dichloromethane/ethanol);

(±)-1,4,5,6-Tetrahydro-2-methyl-4-(2-nitrophenyl)-5-oxo-1,6-naphthyridine-3-carboxylic acid.sodium salt, mp >220° C. (decomp.) (from ethanol);

(±)-1,4,5,6-Tetrahydro-2-methyl-4-(2-nitrophenyl)-5-oxo-1,6-naphthyridine-3-carboxylic acid- (2-methoxyethyl)ester; mp 265° C. (decomp.) (from glacial acetic acid);

(±)-1,4,5,6-Tetrahydro-2-methyl-5-oxo-4-(2-trifluoromethylphenyl)-1,6-naphthyridine-3-carboxylic acid isobutyl ester, mp 169°–170° C. (from methanol);

(±)-1,4,5,6-Tetrahydro-2-methyl-5-oxo-4-(2-trifluoromethylphenyl)-1,6-naphthyridine-3-carboxylic acid isopropyl ester, mp 268°–270° C. (from methanol);

(±)-1,4,5,6-Tetrahydro-2-methyl-4-(3-nitrophenyl)-5-oxo-1,6-naphthyridine-3-carboxylic acid methyl ester, mp 308°–310° C. (decomp.) (from methanol);

(±)-1,4,5,6-Tetrahydro-2-methyl-1-(2-morpholinoethyl)-4-(2-nitrophenyl)-5-oxo-1,6-naphthyridine-3-carboxylic acid methyl ester.hydrochloride, mp 285° C. (decomp.) (from methanol/water);

(±)-6-Benzyl-4-(2,3-dichlorophenyl)-1,4,5,6-tetrahydro-2-methyl-5-oxo-1,6-naphthyridine-3-carboxylic acid methyl ester, mp 145°–148° C. (from ethyl acetate/methanol);

(±)-4-(2,1,3-Benzoxadiazol-4-yl)-1,4,5,6-tetrahydro-2-methyl-5-oxo-1,6-naphthyridine-3-carboxylic acid methyl ester, mp 302°–304° C. (from methanol);

(±)-1,4,5,6-Tetrahydro-2-methyl-4-(3-nitrophenyl)-5-oxo-1,6-naphthyridine-3-carboxylic acid-[2-(N-benzyl-N-methylamino)ethyl]ester, mp 130°–132° C. (decomp.) from ethyl acetate);

(±)-1,4,5,6-Tetrahydro-2-methyl-4-(3-nitrophenyl)-5-oxo-1,6-naphthyridine-3-carboxylic acid-(2-dimethylaminoethyl)ester, mp 215°–217° C. (from diisopropyl ether/ethyl acetate);

(±)-1,4,5,6-Tetrahydro-2-methyl-5-oxo-4-(2-trifluoromethylphenyl)-1,6-naphthyridine-3-carboxylic acid-[2-(N-benzyl-N-methylamino)ethyl]ester;

(±)-1,4,5,6-Tetrahydro-2-methyl-4-(3-nitrophenyl)-5-oxo-1,6-naphthyridine-3-carboxylic acid- (2-methylthioethyl)ester, mp 233°–235° C. (from ethanol);

(±)-2-Ethyl-1,4,5,6-tetrahydro-8-methyl-5-oxo-4-phenyl-1,6-naphthyridine-3-carboxylic acid ethyl ester, mp 205°–207° C. (from ethyl acetate/ethanol).

(±)-1,4,5,6-Tetrahydro-2-methyl-5-oxo-4-(2-trifluoromethylphenyl)-1,6-naphthyridine-3-carboxylic acid-(2-dimethylaminoethyl)ester.

EXAMPLE 2

1,4,5,6-Tetrahydro-6-(3-dimethylamino propyl)-2-methyl-4-(3-nitrophenyl)-5-oxo-1,6-naphthyridine-3-carboxylic acid ethyl ester 6.9 g (19.4 mmol) of 1,4,5,6-tetrahydro-2-methyl-4-(3-nitrophenyl)-5-oxo-1,6-naphthyridine-3-carboxylic acid ethyl ester prepared according to Example 1, and 2.4 g (19.4 mmol) of N,N-dimethylaminopropylchloride are kept at boiling temperature for 48 hours with 10.7 g (77.6 mmol) potassium carbonate in 500 ml acetone. The product is reduced in volume to dryness under vacuum, the residue is taken up in 500 ml water and 500 ml methylene chloride and the organic phase washed with 500 ml water and dried over sodium sulfate. The brown crude product obtained after removing the solvent in vacuo is recrystallized twice from acetonitrile/ethanol. There is obtained 1,4,5,6-tetrahydro-6-(3-dimethylaminopropyl)-2-methyl-4-(3-nitrophenyl)-5-oxo-1,6-naphthyridine-3-carboxylic acid ethyl ester in the form of yellow needles with a melting point of 212°–213° C.

EXAMPLE 3

1,4,5,6-Tetrahydro-4-(3-chlorophenyl)-2-methyl-5-oxo-1,6-naphthyridine-3-carboxylic acid ethyl ester 6.0 g (14.3 mmol) 1,4-dihydro-4-(3-chlorophenyl)-2-(2-dimethylamino ethenyl)-6-methyl pyridine-3,5-dicarboxylic acid diethyl ester are kept for six hours at boiling temperature in a mixture of 60 ml concentrated aqueous ammonia solution and 60 ml ethanol. After cooling, the solution is reduced to half the volume under vacuum. Water is added and the solution is extracted twice with chloroform. The chloroform solution is washed with a small amount of water and dried over sodium sulfate. The residue obtained after distilling off the solvent is chromatographed over silica gel with methylene chloride/methanol.ammonia (9:1, v/v) and recrystallized from methanol. There is obtained 1,4,5,6-tetrahydro-4-(3-chlorophenyl)-2-methyl-5-oxo-1,6-naphthyridine-3-carboxylic acid ethyl ester in form of beige crystals with a melting point of 152°–155° C. (decomposition).

The 1,4-dihydro-4-(3-chlorophenyl)-2-(2-dimethylamino ethenyl)-6-methylpyridine-3,5-dicarboxylic acid diethyl ester used as starting product is prepared as follows:

A solution of 36.4 g (0.1 mol) 1,4-dihydro-4-(3-chlorophenyl)-2,6-dimethyl-pyridine-3,5-dicarboxylic acid diethyl ester and 14.7 g (0.1 mol) dimethylformamide diethylacetal in 100 ml dry dimethylformamide is kept for 16 hours at boiling temperature under nitrogen atmosphere. After cooling, the solvent is distilled off under vacuum and the residue is taken up in toluene and water and extracted. The toluene solution is washed with water for another time and dried over sodium sulfate. After filtration the solution is evaporated in vacuo and the residue crystallized by grinding with petroleum ether. The twice repeated recrystallization from diisopropyl ether yields yellow crystals with a melting point of 131°–132° C.

EXAMPLE 4

1,4,5,6-Tetrahydro-2,6-dimethyl-4-(2-methoxyphenyl)-5-oxo-1,6-naphthyridine-3-carboxylic acid ethyl ester

5.7 g (16.8 mmol) 1,4,5,6-tetrahydro-4-(2-methoxyphenyl)-2-methyl-5-oxo-1,6-naphthyridine-3-carboxylic acid ethyl ester are added to a solution of 0.4 g (17.4 mmol) sodium in 80 ml absolute ethanol while stirring at room temperature. As soon as a clear solution has formed, 2.4 ml (25.3 mmol) dimethylsulfate are added dropwise at room temperature and the mixture is stirred for three hours at room temperature. The reaction mixture is then mixed with 80 ml water and extracted with chloroform. The united organic phases are washed with a small amount of water and dried over $Na_2SO_4$. After removing the solvent the crystalline residue is chromatographed over silica gel with dichloromethane/methanol.ammonia (95:5, v/v) and crystallized from ethylacetate/ethanol (15:2, v/v).

There is obtained 1,4,5,6-tetrahydro-2,6-dimethyl-4-(2-methoxyphenyl)-5-oxo-1,6-naphthyridine-3-carboxylic acid ethyl ester in form of colorless needes with a melting point of 225° C.

The following compounds are obtained in the same way. The process variants of choice for the preparation of the compounds are stated after their melting points.

(a) 1,4,5,6-Tetrahydro-6-(3-dimethylaminopropyl)-2-methyl-5-oxo-4-phenyl-1,6-naphthyridine-3-carboxylic acid ethyl ester, mp 174°–175° C. from ethyl acetate; process (b).

(b) 1,4,5,6-Tetrahydro-4-(3-chlorophenyl)-6-(3-dimethylaminopropyl)-2-methyl-5-oxo-1,6-naphthyridine-3-carboxylic acid ethyl ester, mp 179°–182° C. from acetonitrile; process (b) (c).

(c) 1,4,5,6-Tetrahydro-4-(3-chlorophenyl)-2-methyl-5-oxo-6-(3-piperidinopropyl)-1,6-naphthyridine-3-carboxylic acid ethyl ester, mp 199°–201° C. from acetonitrile; process (b) (c).

(d) 1,4,5,6-Tetrahydro-4-(2-chlorophenyl)-6-(3-dimethylaminopropyl)-2-methyl-5-oxo-1,6-naphthyridine-3-carboxylic acid ethyl ester, mp 229°–230° C. from acetonitrile; process (b).

(e) 1,4,5,6-Tetrahydro-4-(2-chlorophenyl)-2-methyl-5-oxo-6-(3-piperidinopropyl)-1,6-naphthyridine-3-carboxylic acid ethyl ester.½ ethyl acetate, mp 205°–206° C. from ethyl acetate/ethanol; process (b).

(f) 1,4,5,6-Tetrahydro-2-methyl-4-(3-nitrophenyl)-5-oxo-6-(3-piperidinopropyl)-1,6-naphthyridine-3-carboxylic acid ethyl ester, mp 187°–188° C. from acetonitrile; process (a) (b).

(g) 1,4,5,6-Tetrahydro-2-methyl-5-oxo-4-(2-pyridyl)-1,6-naphthyridine-3-carboxylic acid ethyl ester, mp 290° C. (decomposition) from acetonitrile/ethanol; process (b).

(h) 1,4,5,6-Tetrahydro-6-(3-dimethylaminopropyl)-2-methyl-5-oxo-4-(2-pyridyl)-1,6-naphthyridine-3-carboxylic acid ethyl ester, mp 154°–155° C. from ethyl acetate, process (b).

(i) 1,4,5,6-Tetrahydro-2-methyl-5-oxo-6-(3-piperidinopropyl-2-pyridyl-1,6-naphthyridine-3-carboxylic acid ethyl ester; mp 148°–150° C., from ethyl acetate; process (b).

(j) 1,4,5,6-Tetrahydro-2-methyl-4-(2-nitrophenyl)-5-oxo-1,6-naphthyridine-3-carboxylic acid ethyl ester, m.p. 215°–220° C. from ethanol; process (b).

(k) 1,4,5,6-Tetrahydro-6-(3-dimethylaminopropyl)-2-methyl-5-oxo-4-(2-thienyl)-1,6-naphthyridine-3-carboxylic acid ethyl ester, mp 179°–180° C. from ethyl acetate; process (b).

(l) 1,4,5,6-Tetrahydro-6-(3-dimethylaminopropyl)-2-methyl-4-(2-nitrophenyl)5-oxo-1,6-naphthyridine-3-carboxylic acid ethyl ester, mp 235°–236° C. from acetonitrile/diisopropyl ether; process (b).

(m) 1,4,5,6-Tetrahydro-4-(2,3-dichlorophenyl)-6-(3-dimethylaminopropyl)-2-methyl-5-oxo-1,6-naphthyridine-3-carboxylic acid ethyl ester, mp 268°–270° C. from ethyl acetate/ethanol; process (b).

(n) 1,4,5,6-Tetrahydro-4-(2,3-dichlorophenyl)-2,6-dimethyl-5-oxo-1,6-naphthyridine-3-carboxylic acid ethyl ester; mp 294°–295° C. from ethyl acetate/ethanol; process (b).

(o) 1,4,5,6-Tetrahydro-2-methyl-5-oxo-6-(3-piperidinopropyl)-4-(2-thienyl)-1,6-naphthyridine-3-carboxylic acid ethyl ester; mp 173°–174° C. from ethyl acetate; process (b).

(p) 1,4,5,6-Tetrahydro-6-(3-dimethylaminopropyl)-4-(2-methoxyphenyl)-2-methyl-5-oxo-1,6-naphthyridine-3-carboxylic acid ethyl ester, mp 233°–235° C. (decomposition) from ethyl acetate/ethanol; process (b).

(q) 1,4,5,6-Tetrahydro-6-(3-dimethylaminopropyl)-2-methyl-5-oxo-4-(2-trifluoromethylphenyl)-1,6-naphthyridine-3-carboxylic acid ethyl ester; mp 235°–237° C. from ethyl acetate; process (b).

(r) 1,4,5,6-Tetrahydro-2-methyl-5-oxo-6-(3-piperidinopropyl)-4-(2-trifluoromethylphenyl)-1,6-naphthyridine-3-carboxylic acid ethyl ester, mp 204°–205° C. from ethyl acetate/ethanol; process (b).

(s) 1,4,5,6-Tetrahydro-2-methyl-5-oxo-4-(2-trifluoromethylphenyl)-1,6-naphthyridine-3-carboxylic acid ethyl ester, mp 261° C. from ethanol; process (b).

(t) 1,4,5,6-Tetrahydro-2,6-dimethyl-5-oxo-4-(2-trifluoromethylphenyl)-1,6-naphthyridine-3-carboxylic acid ethyl ester, mp 258° C. from ethanol; process (b).

(u) 1,4,5,6-Tetrahydro-2,6-dimethyl-4-(3-nitrophenyl)-5-oxo-1,6-naphthyridine-3-carboxylic acid ethyl ester, mp 255°–257° C. from ethanol; process (a) (b).

(v) 1,4,5,6-Tetrahydro-4-(2,3-dichlorophenyl)-2-methyl-5-oxo-1,6-naphthyridine-3-carboxylic acid ethyl ester, mp 187°–188° C. from ethanol; process (b).

(w) 1,4,5,6-Tetrahydro-2-methyl-5-oxo-4-(2-thienyl)-1,6-naphthyridine-3-carboxylic acid ethyl ester, mp 284°–285° C. from ethanol; process (b).

(x) 1,4,5,6-Tetrahydro-2-methyl-5-oxo-4-phenyl-1,6-naphthyridine-3-carboxylic acid methyl ester, mp 296°–300° C. (decomposition) from methanol; process (b).

(y) 1,4,5,6-Tetrahydro-2-methyl-5-oxo-4-phenyl-1,6-naphthyridine-3-carboxylic acid tert. butyl ester, mp 252°–255° C. (decomposition) from ethyl acetate; process (b).

(z) 1,4,5,6-Tetrahydro-2,6-dimethyl-4-(2-nitrophenyl)-5-oxo-1,6-naphthyridine-3-carboxylic acid ethyl ester, mp 282°–283° C.; process (b).

(a.a) 2-Ethyl-1,4,5,6-tetrahydro-5-oxo-4-phenyl-1,6-naphthyridine-3-carboxylic acid ethyl ester, process (b); mp 144°–146° C. (ethanol).

(a.b) 4-(2,3-Dichlorophenyl)-1,4,5,6-tetrahydro-2-methyl-5-oxo-6-propyl-1,6-naphthyridine-3-carboxylic acid ethyl ester; process (b); mp 264°–265° C. (ethanol).

(a.c) 1,4,5,6-Tetrahydro-2-methyl-5-oxo-4-phenyl-6-propyl-1,6-naphthyridine-3-carboxylic acid ethyl ester; process (b); mp 215°–217° C. (ethanol).

(a.d) 4-(2-Chlorophenyl)-1,4,5,6-Tetrahydro-2-methyl-5-oxo-1,6-naphthyridine-3-carboxylic acid ethyl ester; mp 204°–205° C. (from ethylacetate/ethanol); process (b).

(a.e) 4-(2-Fluorophenyl)-1,4,5,6-tetrahydro-2-methyl-5-oxo-1,6-naphthyridine-3-carboxylic acid ethyl ester; mp 183°–184° C. (from ethylacetate); process (b).

(a.f) 1,4,5,6-Tetrahydro-2-methyl-4-(2-nitrophenyl)-5-oxo-1,6-naphthyridine-3-carboxylic acid methyl ester; mp 293°–295° C. (decomposition) (from acetic acid); process (b).

(a.g) (±)-4-(2-Fluorophenyl)-1,4,5,6-tetrahydro-2-methyl-5-oxo-1,6-naphthyridine-3-carboxylic acid methyl ester; mp 315°–316° C. (decomposition) (from methanol); process (b).

(a.h) (±)-1,4,5,6-Tetrahydro-2-methyl-4-(2-nitrophenyl)-5-oxo-6-propyl-1,6-naphthyridine-3-carboxylic acid methyl ester, mp 274°–276° C. (from methanol); process (b).

(a.i) (±)-4-(2-Bromophenyl)-1,4,5,6-tetrahydro-2-methyl-5-oxo-1,6-naphthyridine-3-carboxylic acid methyl ester; mp 293°–295° C. (decomposition) (from methanol); process (b).

(a.j) (±)-4-(2-Fluorophenyl)-1,4,5,6-tetrahydro-2-methyl-5-oxo-1,6-naphthyridine-3-carboxylic acid tert. butylester; mp 270° C. (decomposition) (from ethylacetate/acetic acid); process (b).

(a.k) (±)-1,4,5,6-Tetrahydro-2-methyl-5-oxo-4-(2-trifluoromethylphenyl)-1,6-naphthyridine-3-carboxylic acid methyl ester; mp 295° C. (from methanol); process (b).

(a.l) (±)-4-(2,3-Dichlorophenyl)-1,4,5,6-tetrahydro-2-methyl-5-oxo-1,6-naphthyridine-3-carboxylic acid methyl ester; mp 318°–320° C. (decomposition) (from methanol); process (b).

(a.m) (±)-4-(2,3-Dichlorophenyl)-1,4,5,6-tetrahydro-2,6-dimethyl-5-oxo-1,6-naphthyridine-3-carboxylic acid methyl ester; mp 290°–291° C. (from methanol); process (b).

(a.n) (±)-4-(2-Fluorophenyl)-1,4,5,6-tetrahydro-6-isopropyl-2-methyl-5-oxo-1,6-naphthyridine-3-carboxylic acid methyl ester; mp 340°–341° C. (decomposition) (from methanol); process (b).

(a.o) (±)-4-(2-Bromophenyl)-1,4-dihydro-6-isopropyl-2-methyl-5-oxo-1,6-naphthyridine-3-carboxylic acid methyl ester; mp 330°–331° C. (decomposition) (from methanol/ethylacetate); process (b).

(a.p) (±)-4-(3-Chloro-2-fluorophenyl)-1,4,5,6-tetrahydro-2-methyl-5-oxo-1,6-naphthyridine-3-carboxylic acid methyl ester; mp 224°–226° C. (decomposition) (from methanol); process (b).

(a.q) (±)-1,4,5,6-Tetrahydro-2-methyl-5-oxo-(3-piperidinopropyl)-4-(2-trifluoromethylphenyl)-1,6-naphthyridine-3-carboxylic acid methyl ester; mp 168°–170° C. (from ethylacetate); process (b).

(a.r) (±)-4-(2-Diethylaminophenyl)-1,4,5,6-tetrahydro-2-methyl-5-oxo-1,6-naphthyridine-3-carboxylic acid methyl ester; mp 151°–152° C. (decomposition) (from ethylacetate); process (b).

(a.s) (±)-1,4,5,6-Tetrahydro-2-methyl-5-oxo-6-propyl-4-(2-trifluoromethylphenyl)-1,6-naphthyridine-3-carboxylic acid methyl ester; mp 286°–288° C. (decomposition) (from methanol); process (b).

(a.t) (±)-4-(2-Chloro-6-fluorophenyl)-1,4,5,6-tetrahydro-2-methyl-5-oxo-1,6-naphthyridine-3-carboxylic acid methyl ester; mp 311°–313° C. (decomposition) (from methanol/water); process (b).

(a.u) (±)-1,4,5,6-Tetrahydro-2-methyl-4-(3-nitrophenyl)-5-oxo-1,6-naphthyridine-3-carboxylic acid-(2-methoxyethyl ester; mp 254°–255° C. (from ethanol); process (b).

(b.b) (±)-2-Amino-1,4,5,6-tetrahydro-5-oxo-4-phenyl-1,6-naphthyridine-3-carboxylic acid ethyl ester; mp 285° C. (decomposition) (from ethanol); process (b).

(b.d) (±)-2-Amino-4-(2-fluorophenyl)-1,4,5,6-tetrahydro-5-oxo-1,6-naphthyridine-3-carboxylic acid ethyl ester; mp 260°–262° C. (decomposition) (from ethanol); process (b).

(b.e) (±)-1,4,5,6-Tetrahydro-2-methyl-4-(2-nitrophenyl)-5-oxo-1,6-naphthyridine-3-carboxylic acid-(2-methoxyethyl) ester; mp 265° C. (from acetic acid); process (b).

(b.f) (±)-6-(2-Ethoxyethyl)-4-(2-fluorophenyl)-1,4,5,6-tetrahydro-2-methyl-5-oxo-1,6-naphthridine-3-carboxylic acid methyl ester; mp 215° C. (decomposition) (from ethylacetate); process (b).

(b.g) (±)-4-(2-Fluorophenyl)-1,4,5,6-tetrahydro-2-methyl-5-oxo-1,6-naphthyridine-3-carboxylic acid sodium salt; 227°–228° C. (from methanol); process (b).

The compounds (a.k), (a.m), (a.n), and (b.d) are quarter hydrates ($\times 0.25$ $H_2O$), the compounds (a.r) and (b.g) are hydrates ($\times H_2O$), and the compound (a.e) contains 0.5 mol ethylacetate ($\times 0.5 \times CH_3CO_2CH_2CH_3$).

The following comparative tests illustrate the pharmacological efficacy of the compounds according to the general formula I:

I. AGGREGATION-INHIBITING EFFECT

Collagen or ADP-induced thrombocyte aggregation in vitro (rat)

The test was carried out according to the method of BORN (Nature 194, 927–929, 1962). Male Sprague Dawley SIV 50 rats, which had a body weight of 200 g, served as blood donors. Blood was withdrawn from the postorbital venous plexus under ether anesthesia. Nine aliquots of blood were mixed with one aliquot of 3.8% (w/v) tri-Na-citrate solution. After low speed centrifugation of the mixture at room temperature, the platelet-rich plasma (PRP corresponding to the erythrocyte-frree supernatant) was removed and adjusted to a standard concentration of 400 000/µl. A universal aggregometer (Braun, Melsungen) connected with an Eppendorf photometer 1100M (Netheler and Hinz, Hamburg) was used as a measuring instrument. In this test portions of 700 µl of platelet-rich plasma (PRP) were equilibrated in the aggregometer at 37° C. for five minutes and then mixed with 58 µl of the test substance solution or with a 0.9% NaCl solution (corresponding to the blank value). After an incubation time of three minutes, the addition of 35 µl collagen suspension (collagen reagent HORM(®), Hormon Chemie, Munich) or 20 µl ADP solution (end concentration in the test $1 \times 10^{-5}$ mol/liter) causes aggregation. A compensation recorder recorded the change in transmission during the following 15 minutes.

The largest change in transmission occurring in this period was called amplitude (amp) of the aggregation curve. Aggregation-inhibiting substances produce a decrease of this amplitude; the inhibitory effect (E) of a substance is calculated according to the following formula:

$$E = (\text{Amp}_{bank\ value} - \text{AMP}_{test\ substance}) / \text{Amp}_{blank\ value} \times 100\ (\%)$$

Dose-effect curves were drawn for calculating the $IC_{50}$ values. The $IC_{50}$ value shows the end concentration of a substance in the test system which results in a decrease of the amplitude by 50%.

Results

A: Collagen-induced thrombocyte aggregation
B: ADP-induced thrombocyte aggregation
A/B: $IC_{50}$ value (mmol/l)·Arith. M±S.D.

| Example Number | A | B |
| --- | --- | --- |
| 4 b. | 0.16 ± 0.01 | 0.41 ± 0.05 |
| c. | 0.06 ± 0.01 | 0.18 ± 0.01 |
| e. | 0.16 ± 0.02 | 0.33 ± 0.02 |
| f. | 0.07 ± 0.01 | 0.24 ± 0.01 |
| 2 | 0.16 ± 0.01 | 0.51 ± 0.04 |
| Verapamil | 0.21 ± 0.02 | 0.56 ± 0.06 |

II. CARDIOVASCULAR EFFECT

1. $Ca^{2+}$ effect on the smooth muscles

Approximately 10 mm long, freshly isolated pieces of the tenia coli (guinea pig) were encircled at both ends with threads and connected with a mechanico-technical transducer in the organ bath (32° C., bubbled through with carbogen). Five to ten mN (0.5–1 p) were selected as mechanical pretension. The Krebs-Henseleit nutrient solution (Ther. 1965) was used for equilibration of the preparation. This solution was exchanged for K+-rich and Ca++-free solution (40 mmol/l) KCl for depolarization of the cell membrane, the NaCl concentration being decreased correspondingly. One mmol/l $CaCl_2$ was added to the nutrient solution under equilibrium conditions, resulting in a contraction of the muscle preparation. After reaching the new equilibration the test substance was added to the organ bath.

After a ten-minute time of action it was tried to compensate a possible inhibitory effect of the test substance by addition of 12.5 mmol/l $CaCl_2$ to the organ bath. The percentage inhibition of the contraction amplitude after a ten-minute time of action of the test substance, related to the amplitude prior to administration of the substance, was calculated as substance effect. Each substance was tested in two preparations.

2. Isolated atriums of guinea pigs

In a thermostated (35° C.) dissecting dish containing modified nutrient solution acc. to Krebs-Henseleit the left atrium was cautiously separated from the ventricle myocardium by means of scissors and a needle with thread passed through the apex of the atrium and knotted. Subsequently, the basis of the atrium was fastened to the hook of a preparation holder and transferred to a thermostated organ bath containing nutrient solution (25 ml, 35° C.). In the organ bath the thread at the apex of the atrium was attached to a mechanicoelectric transducer. Electrical stimulation was effected supramaximally with a frequency of 100 imp/min (stimulation range 2.5 msec). The hook of the preparation holder represented an electrode, whereas the second electrode was designed as field electrode in the preparation holder parallel to the tensioned atrium.

The substances were cumulatively added to the organ bath at intervals of four minutes. The $IC_{50}$ values stated are approximate values from four atriums and show the substance concentration which approximately produced a 50% inhibition of the contraction amplitude.

| Example Number | $ID_{50}$ (mg/kg) (mouse) | | Tenia coli % inhibition ($3 \cdot 10^{-5}$ mol/l) 10 min | Left atrium of guinea pig $IC_{50}$ (mol/l) |
| --- | --- | --- | --- | --- |
| | IV | IG | | |
| 4 b. | 50 | 400 | 57 ± 7 | $3 \times 10^{-4}$ |
| c. | 35 | 600 | 44 ± 6 | $3 \times 10^{-4}$ |
| e. | — | >1600 | 81 ± 5 | $10^{-4}$ |
| f. | 75 | 400 | 79 ± 3 | $10^{-4}$ |
| 2 | 75 | 600 | 88 ± 12 | $3 \times 10^{-4}$ |
| Verapamil | 7.6 | 163 | 100 ($10^{-6}$ mol/l) | $2 \times 10^{-6}$ |

We claim:

1. A method of inhibiting thrombocyte aggregation comprising administering to a host in need thereof an effective amount of a compound of the formula

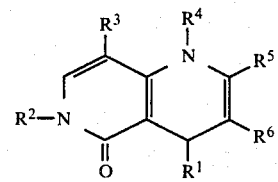

wherein $R^1$ represents phenyl or phenyl substituted in the 2- or 3-position by halogen, nitrogen, methyl, methoxy, difluoromethoxy, trifluoromethoxy, cyano, amino, mono-or dialkylamino having one to six carbon atoms, methylthio or trifluoromethyl, or disubstituted in the 2,3 positions by methoxy or methylenedioxy or in the 2,3 or 2,6 positions by halogen atoms which may be the same or different; unsubstituted pyridyl, thienyl, or 2,1,3-benzoxadiazolyl; $R^2$ is hydrogen, a straight-chained or branched alkyl with up to ten carbon atoms, a group of the formula

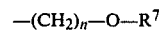

wherein $R^7$ is a straight or branched alkyl group of one to six carbon atoms and n is two or three, or a group of the formula

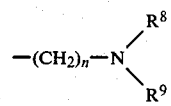

wherein $R^8$ and $R^9$ are each independently a straight or branched alkyl group of one to six carbon atoms or taken together form an alkylene group of four to six carbon atoms, and n is two or three; $R^3$ is hydrogen, a straight-chained or branched alkyl group, or an alkoxycarbonyl radical with up to four carbon atoms; $R^4$ is hydrogen, or a morpholinoethyl group; $R_5$ is a straight-chained or branched alkyl group with up to four carbon atoms, or an amino group; and $R^6$ is a carboxyl group, or an alkyl- or alkyloxyalkyl carbonyl radical, containing up to 12 carbon atoms and optionally interrupted by an oxygen, sulphur, or nitrogen atom; or a pharmacologically acceptable acid addition or base salt thereof together with a pharmaceutically acceptable carrier or diluent.

2. A method of treating pulmonary thrombosis comprising administering to a host in need thereof an effective amount of a compound of the formula

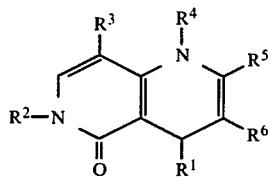

wherein R¹ represents phenyl or phenyl substituted in the 2- or 3-position by halogen, nitro, methyl, methoxy, difluoromethoxy, trifluoromethoxy, cyano, amino, mono-or dialkylamino having one to six carbon atoms, methylthio or trifluoromethyl, or disubstituted in the 2,3 positions by methoxy or methylenedioxy or in the 2,3 or 2,6 positions by halogen atoms which may be the same or different; unsubstituted pyridyl, thienyl, or 2,1,3-benzoxadiazolyl; R² is hydrogen, a straight-chained or branched alkyl with up to ten carbon atoms, a group of the formula —(CH$_2$)$_n$—O—R$^7$ wherein R⁷ is a straight or branched alkyl group of one to six carbon atoms and n is two or three, or a group of the formula

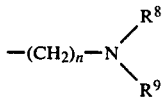

wherein R⁸ and R⁹ are each independently a straight or branched alkyl group of one to six carbon atoms or taken together form an alkylene group of four to six carbon atoms, and n is two or three; R³ is hydrogen, a straight-chained or branched alkyl group, or an alkoxycarbonyl radical with up to four carbon atoms; R⁴ is hydrogen, or a morpholinoethyl group; R⁵ is a straight-chained or branched alkyl group with up to four carbon atoms, or an amino group; and R⁶ is a carboxyl group, or an alkyl- or alkyloxyalkyl carbonyl radical, containing up to 12 carbon atoms and optionally interrupted by an oxygen, sulphur, or nitrogen atom; or a pharmacologically acceptable acid addition or base salt thereof together with a pharmaceutically acceptable carrier or diluent.

* * * * *